(12) United States Patent
Kohnen et al.

(10) Patent No.: US 6,249,707 B1
(45) Date of Patent: Jun. 19, 2001

(54) APPARATUS AND METHOD FOR PERCUTANEOUS IMPLANT OF A PADDLE STYLE LEAD

(75) Inventors: Jane Lambie Kohnen, Minneapolis; Thomas E. Cross, Jr., St. Francis, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/303,045

(22) Filed: Apr. 30, 1999

(51) Int. Cl.⁷ .................................................. A61N 1/05
(52) U.S. Cl. ................................................... 607/117
(58) Field of Search .................................. 607/116, 117, 607/129

(56) References Cited

U.S. PATENT DOCUMENTS

| | | |
|---|---|---|
| 4,141,365 | 2/1979 | Fischell et al. . |
| 4,270,549 * | 6/1981 | Heilman ................ 128/784 |
| 4,285,347 * | 8/1981 | Hess ..................... 128/785 |
| 5,255,691 * | 10/1993 | Otten ..................... 607/117 |
| 5,618,287 * | 4/1997 | Fogarty et al. ........... 606/129 |
| 5,669,882 | 9/1997 | Pyles . |
| 5,762,629 | 6/1998 | Kambin . |

FOREIGN PATENT DOCUMENTS

| | | |
|---|---|---|
| 2688407 | 9/1993 | (FR) . |
| WO9737720 | 10/1997 | (WO) . |

* cited by examiner

*Primary Examiner*—William E. Kamm
(74) *Attorney, Agent, or Firm*—Banner & Witcoff, Ltd.

(57) ABSTRACT

A needle assembly for introduction of a paddle style lead near a spinal column of a patient includes a body having a proximal end and a distal end, a lumen with a continuous oblong cross section, and a paddle style lead adapted to accept a stiffening member. The distal end of the body has an introducer portion where the top side of the introducer has an orifice to allow for protrusion of the paddle style lead from the lumen into the spinal column area. The needle has a hub affixed to the proximal end of the body which is adapted to receive a stylet. The needle may also have a stylet that is inserted within the lumen. The introducer of the needle has a curvature extending from the bottom side toward the top side at the distal end and guides the introduction of the paddle style lead near the spinal column.

22 Claims, 6 Drawing Sheets

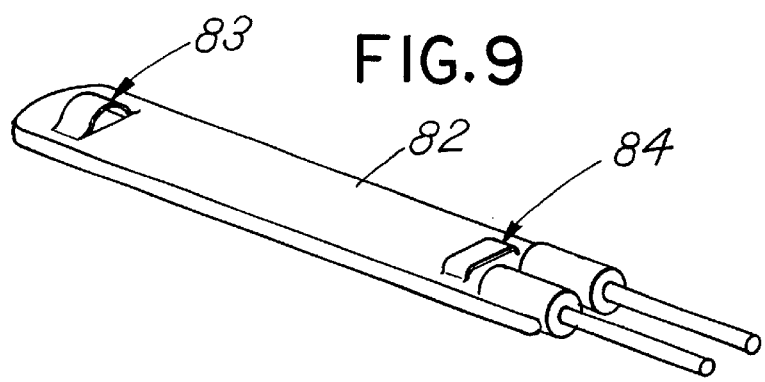
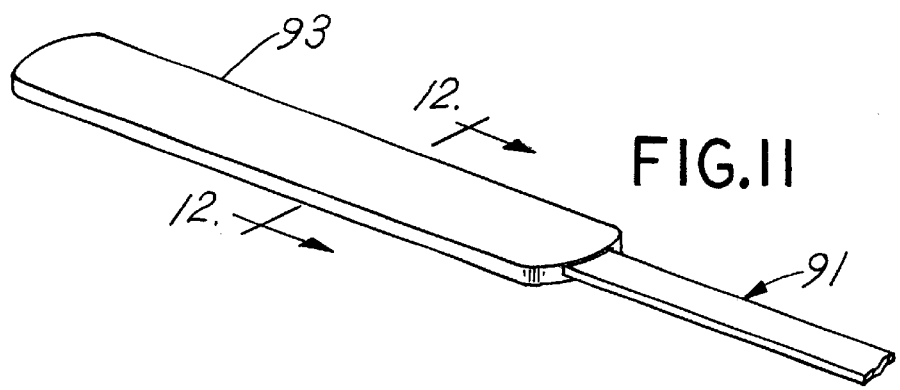
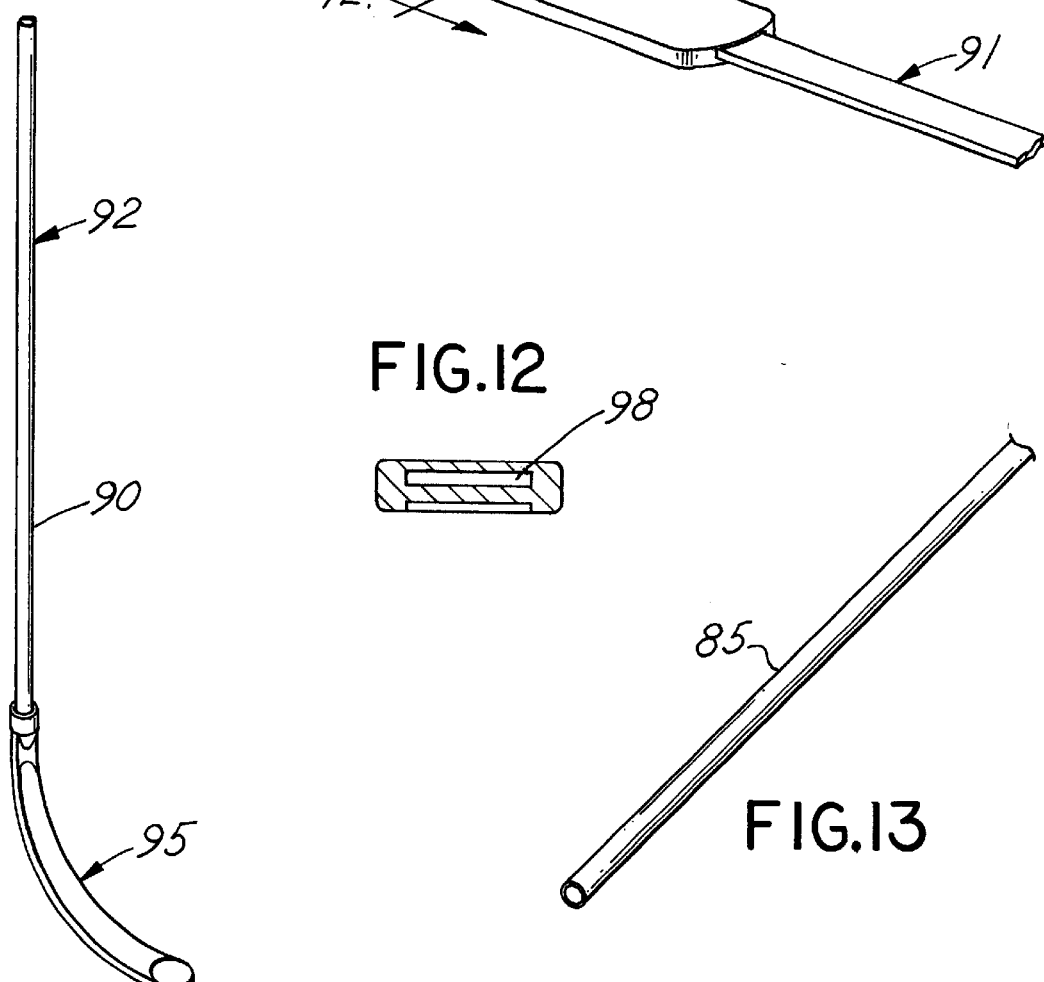

APPARATUS AND METHOD FOR PERCUTANEOUS IMPLANT OF A PADDLE STYLE LEAD

BACKGROUND OF THE INVENTION

1. Field of the Invention

This invention relates generally to a method and apparatus for the percutaneous introduction of a paddle style lead into the space near the spinal cord of a patient. More specifically, this invention relates to the introduction of a paddle style lead whereby the paddle style lead is stiffened during introduction and implantation and becomes flaccid once implanted. Moreover, this invention relates to the percutaneous introduction of the paddle style lead into the spinal column area through a needle with an oblong cross section.

2. Description of Related Art

Spinal cord stimulation is used to treat a multitude of disorders including multiple sclerosis, spinal cord injury, cerebral palsy, amyotrophic lateral sclerosis, dystonia, torticollis and other neurological disorders. Spinal cord stimulation is also useful for treating pain including intractable malignant and nonmalignant pain. Neural stimulation electrodes and leads implanted in the epidural space of the spinal cord of a patient stimulate selected locations of the spinal cord for treatment of pain and various conditions.

Surgically implantable paddle style leads, or flat leads, and percutaneous insertable wire leads for the spinal cord have been in use for some time. These paddle style, or flat leads, and wire leads are used for electrical stimulation of neurons in the spinal cord. Two types of leads are generally used for spinal cord stimulation: 1) wire and 2) paddle.

Typically, a wire lead is introduced into the spinal column using a needle and a stylet assembly. The needle and stylet are inserted into the spinal column area between adjacent vertebrae until the tip of the needle and stylet are advanced into the epidural space of the spinal column area. The stylet is withdrawn and a wire lead is inserted through the open area or lumen of the needle and into the epidural space to a selected location adjacent to the spinal cord. Some needle and stylet assemblies have a curved distal tip to facilitate introduction of the lead at an angle to the axis of the lumen portion of the needle. The needle typically has a side opening or orifice at its distal end for insertion of the lead into the selected location of the spinal cord. In some assemblies, the stylet may fill the entire lumen cavity including the side opening of the needle to prevent the collection of tissue in the lumen cavity during insertion of the needle. The stylet can also provide rigidity to the needle body for use during insertion.

Current needle technology requires that all leads be of a circular cross section in order to be placed through the lumen portion of the needle into the epidural space. Needles used for insertion of the wire leads typically have a circular cross section between 14 and 18 gauge.

The paddle style or flat leads are generally rectangular shaped flat paddles that must be surgically implanted. To introduce a paddle style lead into the epidural space percutaneously using needle insertion, the paddle lead must be rolled to a circular shape to slide through the typical circular cross section needle. The method of rolling the paddle lead and inserting through a needle and unrolling the paddle style lead has not been perfected for use. The only way to insert a paddle style lead is by a surgical procedure known as a laminotomy, a laminectomy, or similar surgical procedure. Because the paddle style lead must be surgically implanted, anesthesiologists may not perform the procedure.

Accordingly, there remains a need in the art for a non-surgical method of inserting a paddle style or flat lead into the spinal cord area.

SUMMARY OF THE INVENTION

The present invention recognizes and provides a solution to the problems associated with the percutaneous introduction of paddle style leads. The invention provides a unique needle for percutaneous insertion of a paddle style lead into the spinal column area. Additionally, the invention provides a method of stiffening the paddle style lead to facilitate insertion of the lead in the spinal column area. Briefly, the present invention comprises a needle for percutaneous insertion having a lumen with an oblong cross section sized to receive a paddle style lead and a temporary stiffening feature for the paddle lead.

Accordingly, an object of the present invention is to provide a non-surgical method and apparatus for percutaneous insertion of paddle style leads that may be utilized by both surgeons and anesthesiologists. Current needles used for introduction of leads for electrical stimulation have a round cross section. Paddle style leads cannot be inserted through these needles. The paddle style lead must be inserted by a surgeon performing a laminotomy, a laminectomy or similar surgical procedure where the surgeon cuts open the tissue and then slides the lead into the proper position. This novel invention uses a needle having a lumen with an oblong cross section. A flat, paddle style lead based on current lead technology is passed through the oblong cross section of the lumen in this needle for introduction into the spinal column area. This invention allows for percutaneous insertion through a needle without performing the above mentioned surgical procedures.

Another object of this invention is to provide a less traumatic procedure for patients during the implantation of paddle style leads for treatment. Surgical introduction of leads for electrical stimulation is traumatic for patients. Insertion of leads for electrical stimulation utilizing an oblong needle that is inserted near the spinal column is less traumatic for patients than surgery where the surgeon must cut the tissue open and then slide the lead into the proper position.

Yet another object of this invention is to provide a method and apparatus for a paddle style lead with a stiffening member to facilitate insertion through the oblong cross section of the lumen of the needle. A stiffening stylet can be used to stiffen the paddle style lead. Another alternative is to use a continuous ribbon style lead such that the cross section of the lead body is the same as the cross section of the paddle. This procedure and apparatus is not limited to use with any specific paddle style or flat lead and can be used for introduction of leads into other areas.

A further object of this invention is to provide a paddle style lead that remains relatively stiff during implantation and positioning and becomes relatively flaccid once inserted. Lead paddles that are stiff during implantation and flaccid while implanted can be a substantial benefit during the introduction of longer lead paddles and as an improvement to current insertion procedures. A stylet, or any other suitable, temporary stiffening method, that may be reversed after implant, will aid the physician in steering the paddle to the desired location and avoid buckling should the physician need to advance the paddle lead from one spinal segment to the next.

Yet another embodiment of this invention is to provide for stiffening the paddle style lead using temperature controlled materials. The lead is composed of at least one temperature controlled material and the temperature controlled material remains relatively stiff when at temperatures below a persons body temperature and the same lead becomes relatively flaccid after heating to at least body temperature after insertion. A relatively stiff paddle improves insertability while a flaccid lead is desired once inserted.

The full range of objects, advantages, and features of the invention are only appreciated by a full reading of this specification and a full understanding of the invention. Therefore, to complete this specification, a detailed description of the invention and the preferred embodiments follow, after a brief description of the drawing wherein additional objects, advantages and features of the invention are disclosed.

BRIEF DESCRIPTION OF THE DRAWINGS

A preferred embodiment of the invention is illustrated in the drawings, wherein like reference numerals refer to like elements in the various views, and wherein:

FIG. 9 is a perspective view of an improved paddle lead adaptable to receive a stiffener strip.

FIG. 10 is a perspective view of a passing elevator stiffening member.

FIG. 11 is a perspective view of a pocket lead with stiffener strip.

FIG. 12 is a cross section view of the pocket lead.

FIG. 13 is a perspective view of a stiffening member.

DESCRIPTION OF THE PREFERRED EMBODIMENTS

Figure 1:
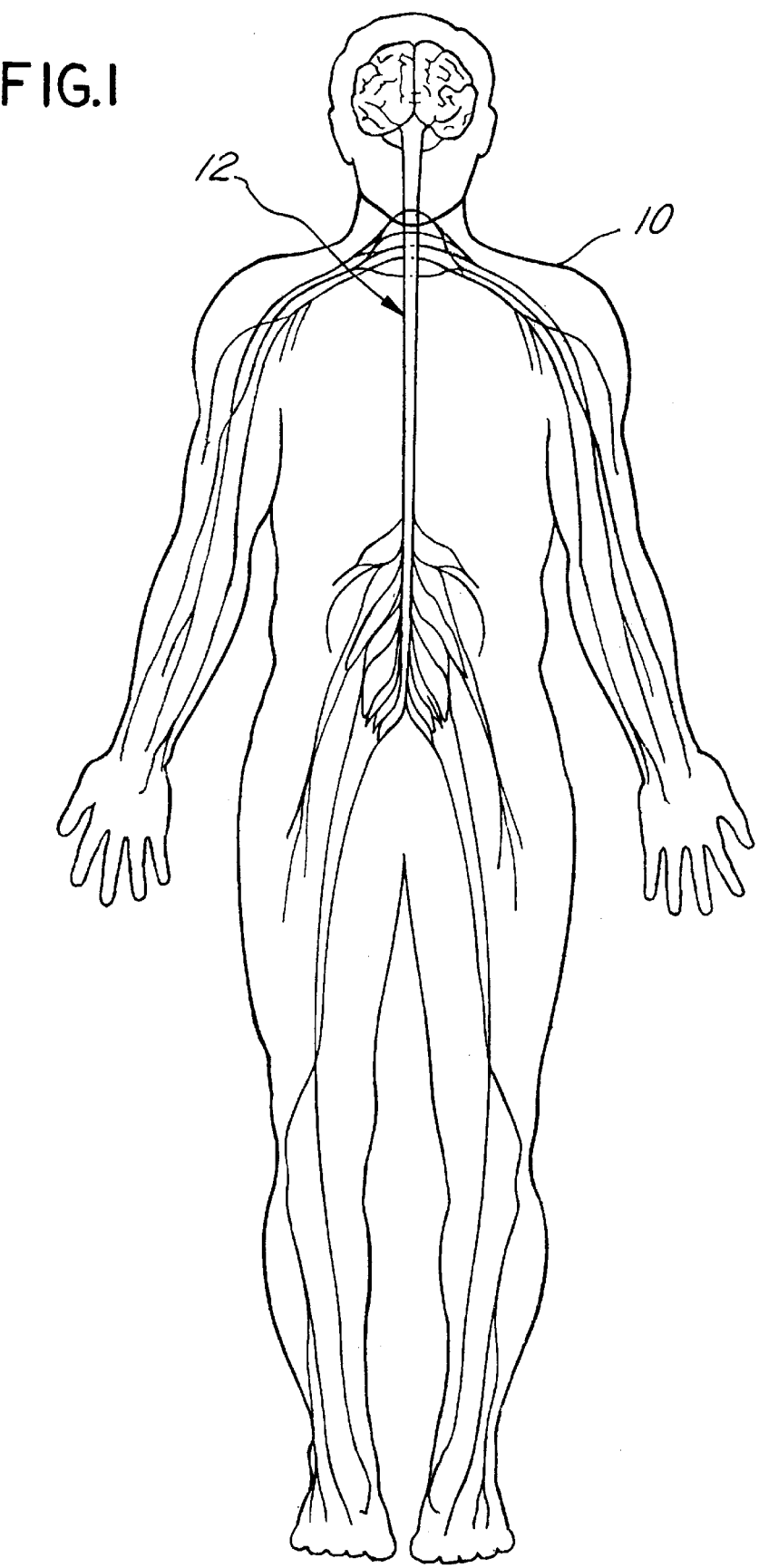
FIG. 1 is a perspective representation in partial cross section of the human body nervous system.
Figure 2:
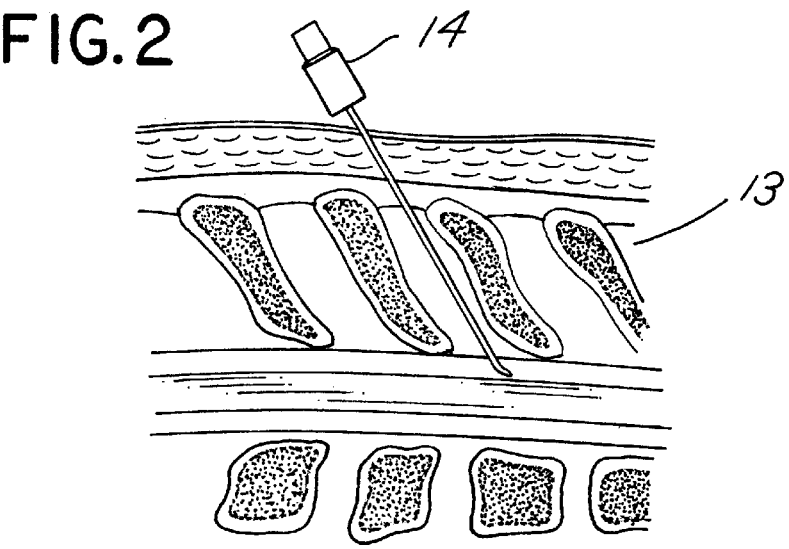
FIG. 2 is a perspective representation in partial cross section of the introduction of the assembled needle within the spinal area.

In the drawings, FIGS. 3–6 illustrate a preferred embodiment of a needle 15 and stylet 45 for use in the procedure for introducing a paddle style lead 55 within the spinal column area 13 as depicted in FIG. 2. The partial cross section of the outline of a human body 10 showing the nervous system including the spinal column 12 is depicted in FIG. 1. The method and apparatus of this invention can be used for the introduction of a paddle style lead 55 into the spinal column area 13 of the nervous system.

Referring to FIG. 2, the assembled needle and stylet 14 are further depicted in relation to the spinal area 13. Needle assembly 14 is inserted into the spinal column area 13 in a fashion generally known in the art. In accordance with the novel improvement of the present invention, lumen 25 of the needle 15 has an oblong cross section sized to insert a paddle style lead and has a curve at the distal end 35 of the needle 15.

Figure 3:
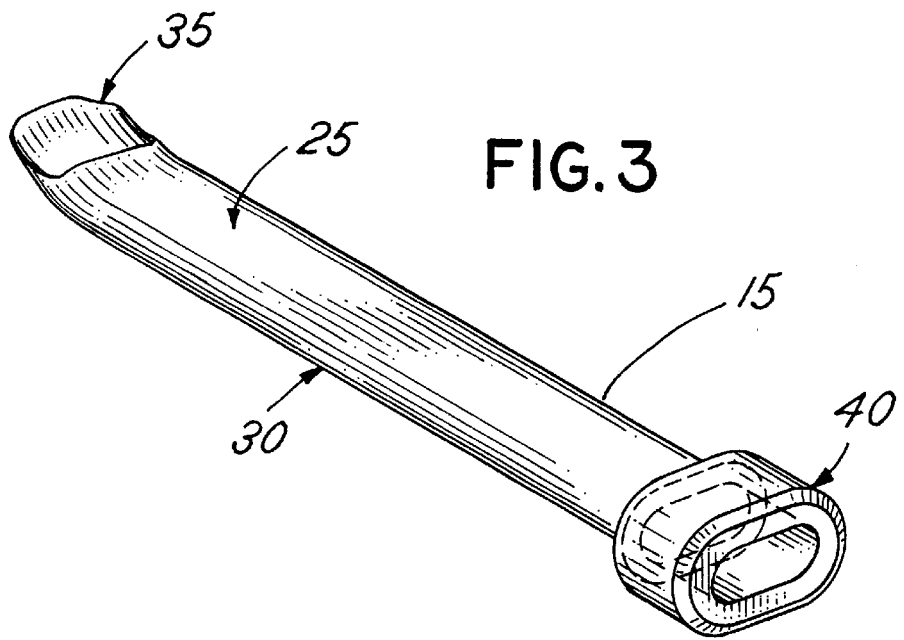
FIG. 3 is a perspective view of the preferred needle of the present invention.

Turning now to FIG. 3, a preferred embodiment of the needle 15 for percutaneous implant of a paddle style lead is depicted in perspective view. The needle 15 comprises a body 30 having a proximal end 40 and a distal end 35 and an inside lumen 25. The lumen 25 has an oblong cross section. The oblong cross section of the lumen 25 is adapted to receive a stylet 45 and a paddle style lead 55. The cross section of the lumen 25 is such that the width is greater than the height. A typical width for the lumen 25 cavity to receive a paddle style lead 55 is 2.5 mm to 12 mm (0.1" to 0.5") with a height of 1.4 mm to 2.0 mm (0.055" to 0.079"). The needle 15 is preferably made of stainless steel or other suitable materials. The needle 15 may also be adapted to insert multiple wire leads. Advantageously, the present invention allows a paddle lead to be inserted percutaneously without requiring the lead to be rolled/contorted to fit the geometry of the needle lumen.

Figure 4:
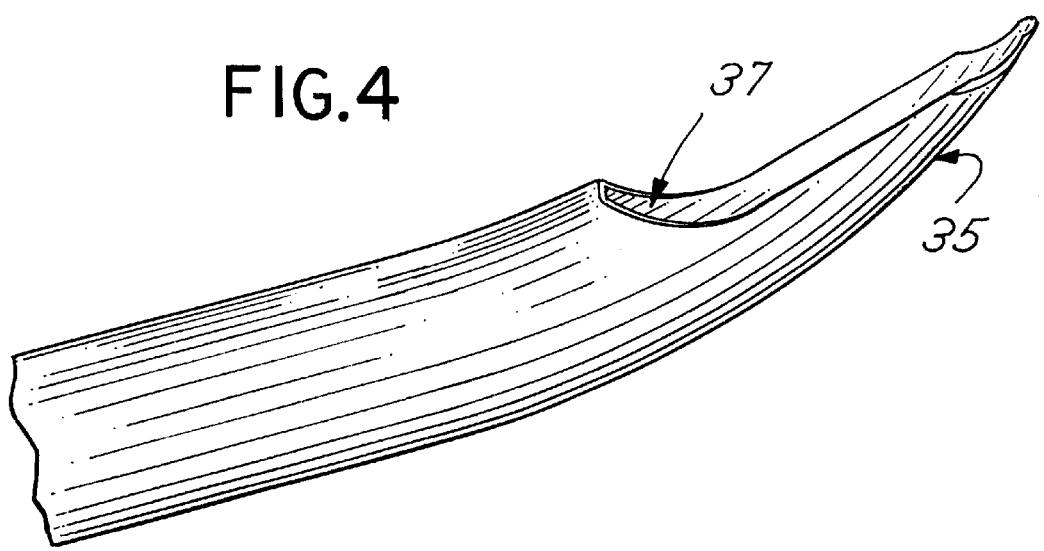
FIG. 4 is a perspective view of the preferred curved tip of the introducer portion of the needle of the present invention.

The needle 15 is further defined by an introducer portion 35 at the body 30 distal end. Referring to FIG. 4, the introducer portion 35 having a top side and a bottom side is shaped to allow for penetration of a patient's skin and other tissue. Typically, an epidural, Tuohy or modified Tuohy needle may be used. The top side of the introducer portion 35 has an orifice 37 to allow the paddle style lead 55 to exit the lumen 25 of the needle 15 within the spinal column area 13 after insertion of the needle 15. The preferred embodiment of the needle 15 has an introducer 35 with a curvature. The curvature extends from the bottom side of the introducer 35 to the top side of the introducer 35 to facilitate and guide the paddle style lead 55 during insertion. As preferred, the radius of curvature for the introducer 35 is approximately 0.9". Those skilled in the art will appreciate that any other curvature may be implanted and still be considered within the scope of the present invention.

Figure 5:
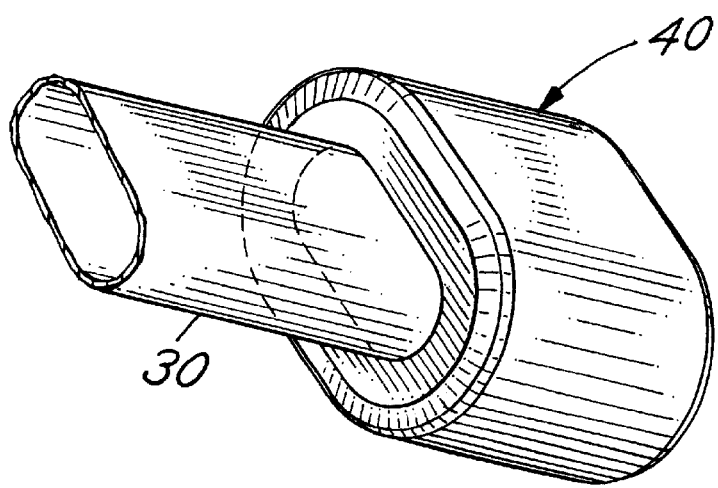
FIG. 5 is a perspective view of the preferred hub of the needle of the present invention.
Figure 15:
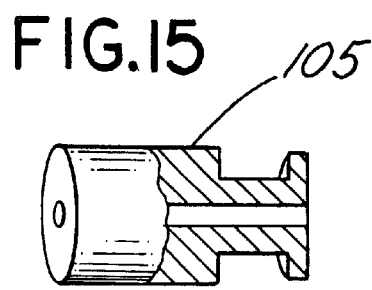
FIG. 15 is a partial cross section perspective view of a Luer lock.
Figure 16:
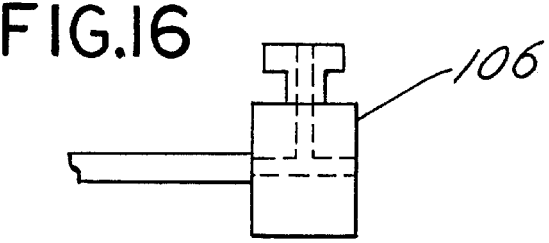
FIG. 16 is a perspective view of an alternative Luer lock.

Referring to FIG. 5, the body 30 proximal end is comprised of a hub 40. The hub 40 is affixed to the proximal end of the body 30 and allows the needle 15 to be grasped. Additionally, the hub 40 provides an interface between the needle 15 and the stylet 45 during insertion. Referring to FIG. 15, an alternative embodiment of the hub 40 comprises a Luer lock 105 to allow for extracting or inserting fluids or for allowing the physician to use the loss of resistance method for identifying the epidural space. Referring to FIG. 16, an alternative embodiment of the Luer lock 106 is depicted.

Figure 6:
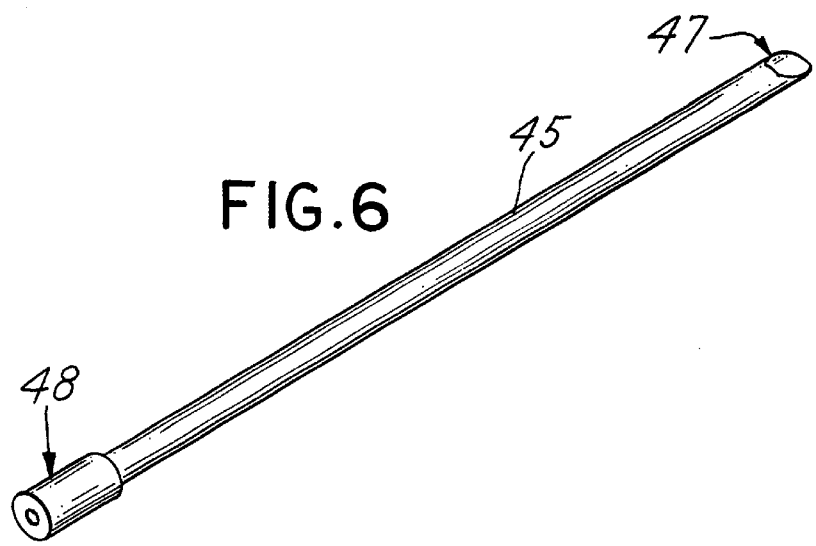
FIG. 6 is a perspective view of the preferred stylet of the present invention.

Turning to now to FIG. 6, it illustrates a perspective view of the stylet 45 having a proximal end that is adapted to mate with the needle hub 40. The stylet 45 may be constructed of stainless steel having a length nearly equivalent to the length of the body 30 of the needle 15. The stylet 45 has a distal tip 47 shaped for matching with the orifice 37 of the introducer 35 of the needle 15. A handle end 48 is affixed to a proximal end of the stylet 45. In the preferred embodiment, the stylet 45 fills the entire orifice 37 of the introducer 35 to prevent any skin or other tissue from entering the lumen 25 during insertion within the patient.

Figure 7:
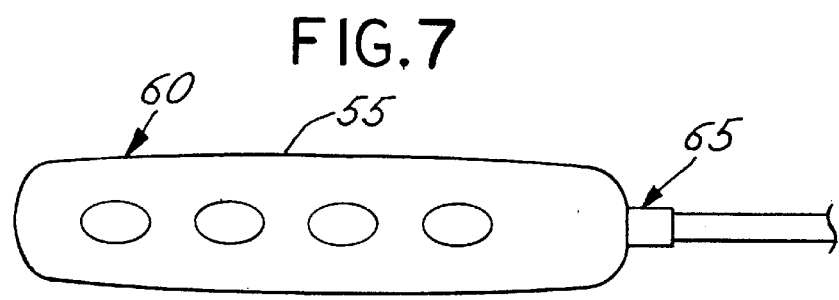
FIG. 7 is a top view of a paddle style lead.

FIG. 7 illustrates a top view of a paddle style lead 55 for electrical stimulation. The paddle style lead 55 is sized such that the width of the paddle style lead 55 is less than the width of the lumen 25 and such that the height of the paddle style lead 55 is less than the height of the lumen 25. The paddle style lead 55 has a lead body 60 and transition area 65. Once inserted in the spinal column area 13, the paddle style lead 55 remains in position and wire leads extend out of the spinal cord typically to a signal generator. The described sizing allows the paddle style lead 55 to be inserted through the lumen 25 into the spinal column area 13 after the needle 15 is inserted in a predetermined position.

Some paddle style leads require stiffening to facilitate insertion into the spinal cord area. The paddle style lead is adapted to accept a stiffening means. The stiffening means provides stiffness to the paddle style lead body during implantation and once implanted the paddle style lead becomes relatively flexible. The stiffening means is only required with the use of a relatively flexible paddle style lead to facilitate insertion into the spinal column area. Any number of techniques can be used to stiffen the paddle style lead, of which the following are examples.

Figure 8:
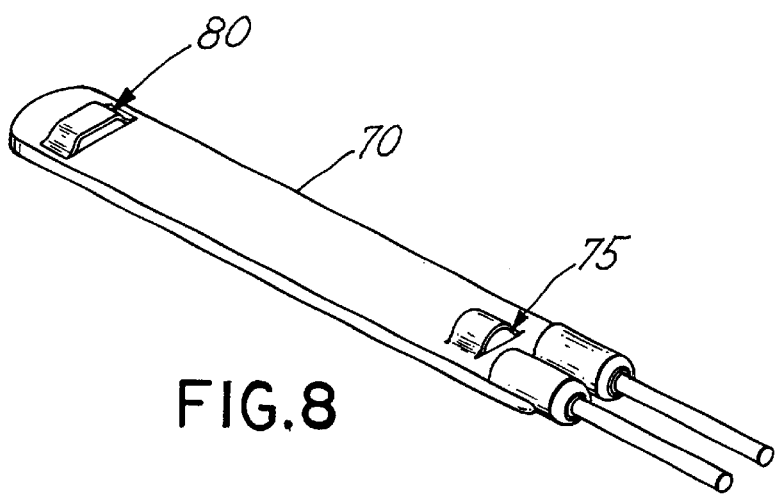
FIG. 8 is a perspective view of an improved paddle lead adaptable to receive a stiffening member during insertion.

FIGS. 8 and 13 illustrate one embodiment of the stiffening means assembly. A paddle style lead 70 is adapted on a first side to accept a stiffening member 85 made of formed wire. The paddle style lead 70 may be a single or a double lead body. A through hole 75 is affixed at a proximal end of the paddle style lead 70 and allows the stiffening member 85 to pass through and continue toward a distal end of the paddle style lead 70. The through hole 75 may be constructed of the same material as the paddle style lead 70 or any other suitable material in the form of a strip. The preferred embodiment is constructed of the same material as the paddle style lead, typically silicone but polyurethane may be used. The strip is shaped to allow the stiffening member 85 to pass into and out of and affix to the paddle style lead 70 on at least two sides. A blind hole 80 is affixed at the distal end of the paddle style lead 70 arranged to allow the stiffening member 85 to pass through the through hole 75 and terminate within the blind hole 80. When fully inserted into the blind hole 80, any further movement of the stiffening member 85 in a direction from the proximal end to the distal end of the paddle style lead 70 pushes the paddle style lead 70 with the stiffening member 85. Once the stiffening member 85 terminates at the blind hole 80, the stiffening member 85 pushes against the blind hole 80 to guide the paddle style lead 70 into a desired position within the spinal column area 13. The paddle style lead 70 remains relatively stiff while the stiffening member 85 is within the through hole 75 and the blind hole 80. The stiffening member 85 is then used to guide the paddle style lead 70 into a predetermined position within the spinal column area 13. After the paddle style lead 70 is in a desired position, the stiffening member 85 is moved in a direction from the distal end to the proximal end of the paddle style lead 70. The stiffening member 85 is not restrained in this direction relative to the movement of the paddle style lead 70. The stiffening member 85 is removeable from the needle 15 while leaving the paddle style lead 70 in the desired position. The paddle style lead 70 is relatively flexible after the stiffening member 85 is removed. A formed wire is the preferred embodiment for use as the stiffening member 85 for insertion of the paddle style lead 70. The stiffening member may also be shaped as a flat strip.

FIG. 10 depicts yet another embodiment of the stiffening means, a passing elevator 90. The passing elevator 90 is constructed of a non-round, elongated length of plastic, typically acetal resin. The passing elevator 90 typically has a generally rectangular cross section. A handle 92 is attached a curved distal end 95. The curved distal end 95 fits within a slot version of the paddle style lead 82 of FIG. 8 as shown in FIG. 9. The blind hole 83 and the through hole 84 are shaped to receive the curved distal end 95 of the passing elevator 90. The passing elevator 90 is restrained in a direction from the proximal end to the distal end of the paddle style lead 82. Once the passing elevator 90 is fully inserted in the slot blind hole 83 of the paddle style lead 82, the paddle style lead 82 moves in conjunction with the passing elevator 90 and allows the paddle style lead 82 to be pulled into a desired position. The passing elevator 90 is not restrained in the opposite direction, allowing the passing elevator 90 to be removed from the patient's body while leaving the paddle style lead 82 in the desired position. An alternative embodiment for stiffening means shown in FIGS. 11 and 12 utilizes a blind hole pocket 98 that extends the length of the pocket paddle style lead 93. A stiffener strip 91 with a continuous cross section is inserted within the pocket 98. The stiffener strip 91 is long and flat and may have a square or rounded end.

Figure 14:
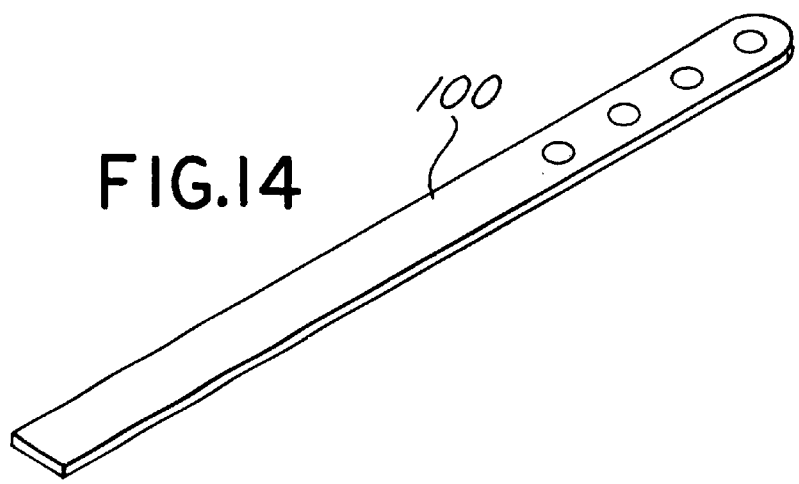
FIG. 14 is a perspective view of a continuous ribbon style paddle lead.

Referring to FIG. 14, a continuous ribbon lead 100 for use with the improved needle for percutaneous insertion is depicted. The continuous ribbon lead 100 may be constructed of silicone that runs the entire length of the lead. The continuous ribbon lead 100 has a continuous cross section with no transition area. The continuous ribbon lead 100 is inserted through the needle 15 of FIG. 2, and the continuous ribbon lead 100 exits the spinal cord to typically a signal generator. The continuous ribbon lead 100 may also be adapted with the stiffening means shown in FIGS. 8,9 and 11.

The description of the apparatus of this invention is not intended to be limiting but is merely illustrative of the preferred embodiment of this invention. Those of ordinary skill in the art will recognize that modifications can be made to the needle and paddle style leads described herein without departure from the true spirit and scope of the invention. For example, the strip of the through hole 75 and blind hole 80 on the paddle style lead 70 may be of alternative shapes to allow for various shaped stiffening members 85.

The true spirit and scope of the inventions of this specification are best defined by the appended claims, to be interpreted in light of the foregoing specification. Other apparatus which incorporate modifications or changes to that which has been described herein are equally included within the scope of the following claims and equivalents thereof. Therefore, to particularly point out and distinctly claim the subject matter regarded as the invention, the following claims conclude this specification.

We claim:

1. A needle assembly for introduction of a paddle style lead near a spinal column of a patient, comprising, in combination:

a body having a proximal end and a distal end, and a lumen having a continuous oblong cross section, the distal end having an introducer portion having a top side and a bottom side, the top side of the introducer having an orifice to allow for protrusion of the paddle style lead from the lumen;

a hub affixed to the proximal end of the body adapted to receive a stylet;

a stylet having a handle end at a proximal end and adapted to be insertable within the lumen; and a paddle style lead having a lead body and wires connected at a transition area adapted to be inserted through the oblong cross section of the lumen, the lead body adaptable to accept a stiffening member.

2. The needle assembly of claim 1, wherein the lead body has a first side and a second side, the first side having a blind hole at a distal end adapted to receive a stiffening member from the proximal end terminating at the blind hole.

3. The needle assembly of claim 1, wherein the lead body has a first side and a second side, the first side having a blind hole at a distal end and a through hole at a proximal end, the blind hole adapted to receive a stiffening member through the through hole terminating at the blind hole.

4. The needle assembly of claim 1, wherein the lead body has an acceptor means affixed to the lead body to allow a stiffening means to mate with the lead body.

5. The needle assembly of claim 1, wherein the lead body has a continuous cross section extending from the lead body to a position outside a patient's body after implantation or to the implanted extension.

6. The needle assembly of claim 1, wherein the lead body is made of at least one temperature controlled material, the at least one temperature controlled material being relatively stiff at a first temperature below a body temperature and relatively flexible at a second temperature at least at the body temperature.

7. The needle assembly of claim 1, wherein the lead body has a first side and a second side, the first side having a pocket substantially the entire length of the paddle style lead adapted to receive a stiffening member.

8. The needle assembly of claim 1, wherein the stiffening member is a passing elevator.

9. The needle assembly of claim 2, wherein the stiffening member is a passing elevator.

10. The needle assembly of claim 7, wherein the stiffening member is a passing elevator.

11. The needle of claim 3, wherein the stiffening member is a formed wire.

12. The needle of claim 3, wherein the stiffening member is a flat strip.

13. The needle of claim 7, wherein the stiffening member is a flat strip.

14. The needle assembly of claim 1, wherein the introducer has a curvature extending from the bottom side toward the top side at the distal end to provide a guide for introduction of the paddle style lead near the spinal column.

15. The needle assembly of claim 1, wherein the hub is a Luer lock.

16. A paddle style lead, comprising, in combination:
   a paddle lead having a first side and a second side, the first side having a blind hole at a distal end and a through hole at a proximal end adapted to receive a stiffening member;
   a stiffening member received through the through hole and terminating at the blind hole.

17. The paddle style lead of claim 16, wherein the stiffening member is a formed wire.

18. The paddle style lead of claim 16, wherein the stiffening member is a passing elevator.

19. The paddle style lead of claim 16, wherein the stiffening member is a flat strip.

20. A paddle style lead, comprising a paddle lead made of at least one temperature controlled material, the at least one temperature controlled material being relatively stiff at a first temperature below a body temperature and relatively flexible at a second temperature at least at the body temperature.

21. A method of introducing a paddle style lead near a spinal column of a patient, comprising the steps of:
   inserting a stiffening member through a through hole on a paddle lead until the stiffening member terminates at a blind hold on a distal end of the paddle lead;
   inserting the paddle lead and the stiffening member near the spinal column of a patient and positioning the paddle lead near a predetermined spinal column area; and
   withdrawing the stiffening member while leaving the paddle lead in the spinal column area.

22. A method of introducing a paddle style lead near a spinal column of a patient, comprising the steps of:
   cooling to a first temperature below body temperature a paddle lead made of at least one temperature controlled material, the at least one temperature controlled material being relatively stiff at a first temperature below a body temperature and relatively flexible at a second temperature at least at the body temperature;
   inserting the cooled paddle lead near the spinal column of a patient positioning the paddle lead to a predetermined spinal column area; and
   heating the paddle lead to at least the body temperature.

\* \* \* \* \*